United States Patent
Park et al.

(10) Patent No.: US 12,358,872 B2
(45) Date of Patent: Jul. 15, 2025

(54) METHOD FOR PRODUCING LAUROLACTAM, DEVICE FOR SYNTHESIZING SAME, LAUROLACTAM COMPOSITION PRODUCED THEREBY, AND METHOD FOR PRODUCING POLYLAUROLACTAM USING SAME

(71) Applicant: HANWHA SOLUTIONS CORPORATION, Seoul (KR)

(72) Inventors: Jinho Park, Daejeon (KR); Jiyeon Kim, Daejeon (KR); Hyun Seo, Daejeon (KR); Namjin Jang, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 516 days.

(21) Appl. No.: 17/782,244

(22) PCT Filed: Oct. 27, 2020

(86) PCT No.: PCT/KR2020/014732
§ 371 (c)(1),
(2) Date: Jun. 3, 2022

(87) PCT Pub. No.: WO2021/112407
PCT Pub. Date: Jun. 10, 2021

(65) Prior Publication Data
US 2023/0020512 A1    Jan. 19, 2023

(30) Foreign Application Priority Data
Dec. 6, 2019   (KR) .................. 10-2019-0161823

(51) Int. Cl.
*C07D 201/04* (2006.01)
*C07D 225/02* (2006.01)

(52) U.S. Cl.
CPC ......... *C07D 201/04* (2013.01); *C07D 225/02* (2013.01)

(58) Field of Classification Search
CPC .................................................. C07D 201/04
See application file for complete search history.

(56) References Cited

U.S. PATENT DOCUMENTS

| 8,309,714 B2 | 11/2012 | Kugimoto |
| 2010/0324283 A1 | 12/2010 | Ishihara |
| 2014/0114062 A1 | 4/2014 | Kugimoto |

FOREIGN PATENT DOCUMENTS

| CN | 102892752 A | 1/2013 |
| CN | 109867616 A | 6/2019 |
| EP | 2292599 A1 | 3/2011 |
| JP | 2002003470 A | 1/2002 |
| KR | 20190052621 A | 5/2019 |
| WO | 2004011428 A1 | 2/2004 |
| WO | 2008012480 A2 | 7/2007 |
| WO | 2019098569 A1 | 5/2019 |
| WO | 2019098570 A1 | 5/2019 |

OTHER PUBLICATIONS

The First Office Action issued on Dec. 14, 2023.
European search report issued on Dec. 8, 2023.
J. Am. Chem. Soc. 2005, v.127, pp. 11240-11241.
An office action issued on Jul. 12, 2023 for corresponding JP Patent Application.

*Primary Examiner* — Bruck Kifle
(74) *Attorney, Agent, or Firm* — Harvest IP Law, LLP

(57) ABSTRACT

Provided are a method of preparing laurolactam including: a) synthesizing laurolactam by Bechmann rearrangement of cyclododecanone oxime under a catalyst system, b) mixing the laurolactam synthesized in a) with a good solvent and removing the catalyst system, and c) mixing the laurolactam from which the catalyst system has been removed in b) with a poor solvent and performing recrystallization, a synthesis device thereof, a laurolactam composition prepared therefrom, and a method of preparing polylaurolactam using the laurolactam composition.

7 Claims, No Drawings

METHOD FOR PRODUCING LAUROLACTAM, DEVICE FOR SYNTHESIZING SAME, LAUROLACTAM COMPOSITION PRODUCED THEREBY, AND METHOD FOR PRODUCING POLYLAUROLACTAM USING SAME

CROSS-REFERENCE TO RELATED APPLICATIONS

This application is a National Stage of International Application No. PCT/KR2020/014732 filed Oct. 27, 2020, claiming priority based on Korean Patent Application No. 10-2019-0161823 filed Dec. 6, 2019, the disclosure of which is incorporated herein by reference in its entirety.

TECHNICAL FIELD

The present invention relates to a method of preparing laurolactam, a synthesis device thereof, a laurolactam composition prepared thereby, and a method of preparing polylaurolactam using the same.

BACKGROUND ART

In general, a method of industrially preparing an amide compound involves converting a corresponding oxime compound using Bechmann rearrangement. For example, laurolactam may be synthesized by Bechmann rearrangement of cyclododecanone oxime. However, a process of Bechmann rearrangement is a significantly complicated process, and uses a concentrated sulfuric acid and oleum, which are strong acids and are required to have a high content, so that a large amount of an ammonium sulfate by-product is produced during neutralization, and thus, the process has a limitation in the need for equipment for treating the by-product. In addition, Bechmann rearrangement is performed in a solvent, and cyclododecanone oxime should have a high solubility in the solvent and the solvent should correspond to those which do not react with the concentrated sulfuric acid and the oleum as a catalyst, and thus, the selection of the solvent is limited.

Meanwhile, a polymer material such as an aliphatic carbonate-based polymer and polylaurolactam may be synthesized by anionic polymerization of monomers such as laurolactam, and the purity of a laurolactam monomer has a significant effect on polymerization reaction activity. Conventionally, laurolactam was purified by preparing a reaction product including laurolactam in Bechmann rearrangement, removing the used solvent by distillation, and then removing heavies in a solid phase and/or a liquid phase, but a small amount of a catalyst remains in a final laurolactam product to rapidly decrease the activity of the anionic polymerization reaction. Accordingly, a solution to remove the catalyst remaining after Bechmann rearrangement by a simplified process to purify high-purity laurolactam and increase anionic polymerization activity of a laurolactam monomer and the like is demanded.

DISCLOSURE

Technical Problem

An object of the present invention is to provide a method of preparing laurolactam by Bechmann rearrangement of cyclododecanone oxime, and purifying the synthesized laurolactam by a simplified process, thereby removing a remaining catalyst and preparing high-purity laurolactam.

Another object of the present invention is to provide a synthesis device of the laurolactam.

Another object of the present invention is to provide a laurolactam composition synthesized by the method of preparing laurolactam.

Still another object of the present invention is to provide a method of preparing polylaurolactam with a high conversion rate, using an anionic polymerization reaction of the synthesized laurolactam.

Technical Solution

In one general aspect, a method of preparing laurolactam includes: a) synthesizing laurolactam by Bechmann rearrangement of cyclododecanone oxime under a catalyst system, b) mixing the laurolactam synthesized in step a) with a good solvent and removing the catalyst system, and c) mixing the laurolactam from which the catalyst system has been removed in step b) with a poor solvent and performing recrystallization.

In step a), the Bechmann rearrangement may be synthesis of laurolactam from cyanuric chloride by a catalyst system including cyanuric chloride (TCT) and zinc chloride ($ZnCl_2$), in the presence of a solvent including isopropyl-cyclohexane (IPCH).

Step a) may further include removing the solvent by distilling the synthesized laurolactam.

In step b), the catalyst system may be removed using a difference in solubility of the catalyst system and the laurolactam in the good solvent.

The good solvent may be a C1 to C4 hydrocarbon organic solvent containing one or two or more functional groups selected from the group consisting of a hydroxyl group, an amine group, and a thiol group.

In step c), the laurolactam may be recrystallized using a difference in solubility of laurolactam in the good solvent and the poor solvent.

The good solvent and the poor solvent may be miscible.

The poor solvent may be distilled water or deionized water.

The good solvent and the poor solvent may be injected at a weight ratio of 1:1.5 to 1:3.

A step of evaporating the recrystallized laurolactam to remove heavies in a liquid phase and/or a solid phase and separating laurolactam in a gas phase may be further included.

In another general aspect, a laurolactam synthesis device includes: a first reactor for synthesizing laurolactam by Bechmann rearrangement of cyclododecanone oxime under a catalyst system, an evaporator for removing a solvent from the laurolactam synthesized in the first reactor, a second reactor for mixing the laurolactam from which the solvent has been removed in the evaporator with a good solvent and removing the catalyst system, and a third reactor for mixing the laurolactam from which the catalyst system has been removed in the second reactor with a poor solvent and performing recrystallization.

A filter for removing the catalyst system precipitated in the second reactor may be further included.

A film evaporator for separating heavies from the recrystallized laurolactam may be further included.

In another general aspect, a laurolactam composition synthesized by the method of preparing laurolactam is provided.

The laurolactam composition may include the catalyst system used in the Bechmann rearrangement at 5 wt % or less with respect to the total weight of the laurolactam composition.

In still another general aspect, a method of preparing polylaurolactam includes: anionically polymerizing the laurolactam composition in the presence of an anionic initiator to prepare polylaurolactam.

The anionic initiator may include one or two or more selected from the group consisting of NaH, n-BuLi, KH, and LiH.

The anionic polymerization may be performed at 250 to 350° C. for 10 to 60 minutes.

The polymerized polylaurolactam may have a weight average molecular weight of more than 6,000.

Advantageous Effects

After laurolactam is synthesized by Bechmann rearrangement, a catalyst system and a solvent remaining in a reaction product may be effectively removed only by a simplified process.

An anionic polymerization reaction may be performed with a high conversion rate, using a purified laurolactam monomer.

BEST MODE

Hereinafter, the present invention will be described in detail. Terms used in the present specification should be interpreted as having the meaning commonly understood by a person skilled in the art, unless otherwise defined. Drawings and examples of the present specification are for a person with ordinary skill in the art to easily understand and carry out the present invention, descriptions which may obscure the gist of the present invention may be omitted in the drawings and the examples, and the present invention is not limited by the drawings and the examples.

The singular form of the term used in the present invention may be construed as including a plural form also, unless otherwise particularly described.

A catalyst system in the specification of the present invention may refer to a composite catalyst system including two or more compounds, for example, a catalyst system including a main catalyst and a co-catalyst.

Hereinafter, a method of preparing laurolactam according to an exemplary embodiment will be described.

The method of preparing laurolactam includes: a) synthesizing laurolactam by Bechmann rearrangement of cyclododecanone oxime under a catalyst system, b) mixing the laurolactam synthesized in step a) with a good solvent and removing the catalyst system, and c) mixing the laurolactam from which the catalyst system has been removed in step b) with a poor solvent and performing recrystallization.

Step a) is a step of synthesizing laurolactam by Bechmann rearrangement of cyclododecanone oxime under a catalyst system, and the Bechmann rearrangement may be synthesis of laurolactam from cyclododecanone oxime by a catalyst including cyanuric chloride (TCT) and zinc chloride ($ZnCl_2$) in the presence of a solvent.

Specifically, in step a), the Bechmann rearrangement may be performed at a temperature of 70 to 130° C., preferably 90 to 110° C., and more preferably 95 to 100° C. for 1 to 20 minutes, preferably 5 to 20 minutes, and more preferably 5 to 15 minutes. In the reaction, when a reaction temperature is too high, a large amount of by-products such as heavies is produced, and when a reaction temperature is too low, a reaction rate is not sufficiently rapid, and application to a commercial process is difficult. In addition, when a reaction time is less than 1 minute, cyclododecanone oxime may not be sufficiently rearranged into laurolactam, and when a reaction time is more than 20 minutes, by-products are excessively produced, which is not preferred.

Meanwhile, the Bechmann rearrangement refers to rearrangement of keto oxime into an acid amide, and in particular, in the present invention, may refer to a reaction of rearrangement of the cyclododecanone oxime into laurolactam.

The catalyst system may include cyanuric chloride (TCT) and zinc chloride ($ZnCl_2$), in which cyanuric chloride and the like are used as a main catalyst and zinc chloride may be used with the main catalyst as a co-catalyst. Specifically, the main catalyst and the co-catalyst may be included at 0.1 to 10 parts by weight, preferably 0.1 to 5 parts by weight, and more preferably 0.5 to 2 parts by weight, with respect to 100 parts by weight of cyclododecanone oxime. When the content of the catalyst system is too low, Bechmann rearrangement may not be sufficiently performed, and when the content of the catalyst system is too high, a catalyst system material remains at a high content in a reaction product after completion of the reaction, and thus, it is difficult to effectively remove the catalyst system.

More specifically, the catalyst system may include cyanuric chloride and zinc chloride at a weight ratio of 2:1 to 1:1, preferably at a weight ratio of 1.5:1 to 1:1, and more preferably at a weight ratio of 1.3:1 to 1:1. Thus, a decrease in a conversion rate depending on a moisture content limited by the Bechmann rearrangement may be suppressed to effectively synthesize laurolactam, and after completion of the reaction, the catalyst system remaining in a reaction product may be easily removed only by a simplified process.

The solvent is preferably, for example, an organic solvent including isopropylcyclohexane (IPCH). The solvent may be successfully used to prepare laurolactam from cyclododecanone oxime using Bechmann rearrangement by a strong non-polarity characteristic, and a solvent may be easily removed by distilling a reaction product by the characteristic of having a large difference in a boiling point from the reaction product. Therefore, high-purity laurolactam may be effectively prepared.

The organic solvent including IPCH may be used at 30 to 50 parts by weight with respect to 100 parts by weight of cyclododecanone oxime. When the organic solvent is included in the above content range, it is easy to perform the Bechmann rearrangement of cyclododecanone oxime, and the solvent may be easily removed by distilling the reaction product. Therefore, high-purity laurolactam may be effectively prepared.

Subsequently, step b) is a step of mixing laurolactam synthesized in step a) with a good solvent and removing the catalyst system, and the good solvent may be a C1 to C4 hydrocarbon organic solvent containing one or two or more functional groups selected from the group consisting of C1 to C4 hydrocarbon organic solvents, preferably a hydroxyl group, an amine group, and a thiol group, and more preferably, a C1 to C4 hydrocarbon containing a hydroxyl group, or a C1 to C4 alcohol.

When the good solvent is mixed, the catalyst system may be removed using a difference in solubility of the catalyst system and laurolactam in the good solvent. Specifically, the catalyst system is not dissolved in the good solvent and is precipitated as solid particles, but laurolactam has high solubility in the good solvent, and thus, is all substantially dissolved in the good solvent and may not be precipitated.

Thereafter, the catalyst system precipitated as particles may be easily removed with a filter. Here, when the good solvent is injected in too small an amount, a part of laurolactam, which is not dissolved and is present as a solid, may be removed from a filter together with a residual catalyst, thereby decreasing a laurolactam yield, and the part of laurolactam which is not dissolved in the good solvent is agglomerated with a residual catalyst system, passes the filter, and remains. On the contrary, when the good solvent is injected in too large an amount, it may not be easy to perform the recrystallization of laurolactam in step c). Therefore, the laurolactam synthesized in step a) and the good solvent may be mixed at a weight ratio of 1:4 to 1:7, preferably at a weight ratio of 1:5 to 1:7, and more preferably at a weight ratio of 1:6 to 1:7.

Meanwhile, in the specification of the present invention, the good solvent may refer to a solvent which has high affinity with laurolactam (solute) and may dissolve laurolactam well, and the poor solvent may refer to a solvent which has low affinity with laurolactam and does not dissolve laurolactam well.

Continuously, in step c), the laurolactam from which the catalyst system has been removed in step b) is mixed with the poor solvent and is recrystallized, and as the poor solvent, a material miscible with the good solvent may be adopted, and specifically distilled water or deionized water may be used. When the poor solvent is mixed, laurolactam may be recrystallized using a difference in solubility of laurolactam in the good solvent and the poor solvent. Specifically, the laurolactam has a characteristic of having high solubility in the good solvent and low solubility in the poor solvent, and when the poor solvent is mixed with the good solvent in which laurolactam is dissolved in step b), the concentration of the good solvent is decreased to decrease the solubility of laurolactam, and as a result, laurolactam is recrystallized and precipitated as a solid.

The good solvent and the poor solvent may be injected, for example, at a weight ratio of 1:1.5 to 1:3, preferably at a weight ratio of 1:2 to 1:3, and more preferably at a weight ratio of 1:2 to 1:2.5. When the good solvent is injected in excess as compared with the poor solvent, a part of laurolactam is not precipitated as a solid and may be present in a state of being dissolved in the good solvent, and the yield of purified laurolactam may be lowered, which is thus not preferred.

Subsequently, a step of evaporating the recrystallized laurolactam to remove heavies in a liquid phase and/or a solid phase and separating laurolactam in a gas phase may be further performed. As a result, high-purity laurolactam may be purified, which is thus preferred.

The evaporation may be performed in a film evaporator, but the present invention is not limited thereto.

Meanwhile, the film evaporator is an evaporation device which is used to obtain a desired material with a high purity from mixed materials (liquid) by a distillation reaction. That is, it forms a thin film of a liquid mixture by a physical force to maximize a surface area of a mixture, thereby increasing an evaporation rate and separating the material with a high purity.

In addition, the present invention may provide a laurolactam synthesis device according to the method of preparing laurolactam described above. In this case, since the technical idea corresponds to the technical idea which is substantially the same as the description for the method of preparing laurolactam, the material used, the reaction conditions, and the like should be interpreted as being substantially the same as the above description, of course.

Hereinafter, the laurolactam synthesis device according to another exemplary embodiment will be described.

The laurolactam synthesis device according to the present invention includes: a first reactor for synthesizing laurolactam by Bechmann rearrangement of cyclododecanone oxime under a catalyst system, an evaporator for removing a solvent from the laurolactam synthesized in the first reactor, a second reactor for mixing the laurolactam from which the solvent has been removed in the evaporator with a good solvent and removing the catalyst system, and a third reactor for mixing the laurolactam from which the catalyst system has been removed in the second reactor with a poor solvent and performing recrystallization.

The laurolactam synthesis device may further include a filter for removing the catalyst system of the solid precipitated in the second reactor.

The laurolactam synthesis device may further include a film evaporator for separating heavies from the recrystallized laurolactam.

As the "reactor", the "(film) evaporator", and the "filter" mentioned in the present invention, various known reactors, (film) evaporators, and filters may be used, and their specification and size may be appropriately adjusted depending on the scale and the environment of the process, and thus, are not limited. In addition, materials may be introduced to each of the reactor, the (film) evaporator, and the filter, or various inlet pipes, outlet pipes, and the like for introducing the materials may be provided in each of the reactor, the (film) evaporator, and the filter, and it may be appropriately adjusted by a person skilled in the art to use various devices for adjusting the inflow and outflow amounts thereof and various devices for controlling the devices.

Hereinafter, a laurolactam composition synthesized by the method of preparing laurolactam according to another exemplary embodiment is provided.

The laurolactam composition has a conversion rate of cyclododecanone oxime of 98 to 99%, preferably 99 to 99.5%, and more preferably 99.5 to 99.9%, and a selectivity of laurolactam of 97 to 98%, preferably 98 to 99%, and more preferably 99 to 99.5%.

In addition, the laurolactam composition may include the catalyst system used in the Bechmann rearrangement at 5 wt % or less, preferably at less than 5 wt %, more preferably at 3 wt % or less, and most preferably at 1 wt % or less, or 0.5 wt % or less. When the content range of the catalyst system is exceeded, the activity of the anionic initiator used in anionic polymerization is significantly decreased, and thus, it is not easy to perform a polymerization reaction.

Meanwhile, the content of the catalyst system included in the laurolactam composition may be measured with an inductively coupled plasma spectrometer (ICP) analyzer.

Hereinafter, another exemplary embodiment provides a method of preparing polylaurolactam, and the method may include anionic polymerization of the laurolactam composition in the presence of an anionic initiator.

Polymerization of the purified laurolactam and an optional new monomer (comonomer) may be performed at 200 to 350° C. for 10 to 60 minutes. Specifically, the polymerization reaction may be performed at 200 to 300° C., preferably at 220 to 250° C. for 10 to 60 minutes, preferably for 10 to 50 minutes, and more preferably for 20 to 40 minutes.

The polymerized polylaurolactam may be a laurolactam-containing polymer, for example, a copolyamide or a polyether-block amide, and preferably, may be polyamide 12 (nylon 12).

The anionic initiator may include, specifically, one or two or more selected from the group consisting of NaH, LiH, KH, and n-BuLi. The catalyst system material used in the Bechmann rearrangement according to an exemplary embodiment of the present invention is known to significantly kill the activity of the anionic initiator, but in the method of preparing laurolactam according to an exemplary embodiment of the present invention and the laurolactam therefrom, the catalyst system is very effectively removed, and thus, the laurolactam monomer may be anionically polymerized in a high polymerization degree in the presence of the anionic initiator.

The anionic polymerization may be performed in a batch reactor or a continuous reactor (CSTR, PFR, or PBR), and preferably, may be performed in a continuous reactor, but the present invention is not limited thereto.

The polymerized polylaurolactam may have a weight average molecular weight of more than 6,000, preferably 6,500 to 14,000, more preferably 8,000 to 12,000, or 9,000 to 11,000.

Hereinafter, the present invention will be described in detail by the examples, however, the examples are for describing the present invention in more detail, and the scope of the present invention is not limited to the following Examples.

EXAMPLES

Preparation Example 1

3 g of cyclododecanone oxime, 12 g of isopropylcyclohexane, 0.045 g of cyanuric chloride, and 0.03 g of zinc chloride were added to a 100 ml round flask. Then, the temperature was adjusted to 95° C. using a heating mantle, and the reaction was performed by stirring at 200 rpm or more. A reaction completion time was 5 minutes, the conversion rate of cyclododecanone oxime was 99% or more, and the selectivity of laurolactam was 99% or more.

Example 1

100 g of the product of Preparation Example 1 was injected into an evaporator, and was distilled at 150° C. to remove IPCH from the top of the evaporator. 700 g of ethanol was injected into a produced brown solid (laurolactam before purification) and dissolved in a flask. Floating solid (catalyst) was removed using a 0.22 μm filter, and 1,600 g of water was injected into laurolactam (LL) dissolved in ethanol to recrystallize a LL solid. A solid was separated from the recrystallized LL using a filter, a film evaporator was used to remove heavies from the bottom, LL was removed from the top, and a residual catalyst content and a LL yield were measured and are shown in the following Table 1.

Subsequently, 50 g of LL and a catalyst were added to a 100 ml round flask at a weight ratio of LL:NaH:ethylene bis stearamide (EBS):tetraethyl orthosilicate (TEOS):$CO_2$=100: 0.6:0.36:0.15:0.15, using the prepared LL, anionic polymerization reaction was performed at 240° C. for 30 minutes to prepare PA 12 (polyamide 12), and the polymerization degree of PA 12 is shown in the following Table 1.

Example 2

The process was performed in the same manner as in Example 1, except that 300 g of ethanol was injected, thereby separating LL, and a residual catalyst content and a LL yield were measured and are shown in the following Table 1, respectively.

Subsequently, an anionic polymerization reaction was performed in the same manner as in Example 1 to prepare PA 12, and the polymerization degree of PA 12 is shown in the following Table 1.

Example 3

The process was performed in the same manner as in Example 1, except that 700 g of water was injected into laurolactam (LL) dissolved in ethanol, thereby separating LL, and a residual catalyst content and a LL yield were measured and are shown in the following Table 1, respectively.

Subsequently, an anionic polymerization reaction was performed in the same manner as in Example 1 to prepare PA 12, and the polymerization degree of PA 12 is shown in the following Table 1.

Comparative Example 1

100 g of the product of Preparation Example 1 was injected into an evaporator, and was distilled at 150° C. to remove IPCH from the top of the evaporator. A film evaporator was used to remove heavies from the produced brown solid in the bottom, LL was removed from the top, and a residual catalyst content and a LL yield were measured and are shown in the following Table 1, respectively.

Subsequently, an anionic polymerization reaction was performed in the same manner as in Example 1 to prepare PA 12, and the polymerization degree of PA 12 is shown in the following Table 1.

Comparative Example 2

The process was performed in the same manner as in Example 1, except that water was not injected into laurolactam (LL) dissolved in ethanol, thereby separating LL, and a residual catalyst content and a LL yield were measured and are shown in the following Table 1, respectively.

Subsequently, an anionic polymerization reaction was performed in the same manner as in Example 1 to prepare PA 12, and the polymerization degree of PA 12 is shown in the following Table 1.

\* Method of Measuring Content of Residual Catalyst System

Since laurolactam is a solid at room temperature, it is not distinguished from a solid catalyst used in the synthesis, but when it is dissolved at 150° C., the catalyst remains as a black solid, and thus, it may be confirmed whether the solid catalyst remains. The weight of the catalyst remaining in the laurolactam prepared in Preparation Example 1 was measured after separating the catalyst as a solid at a high temperature, or using a solvent which may dissolve laurolactam.

\* Method of Measuring Yield of Laurolactam 100 g of the product of Preparation Example 1 was measured GC to calculate the content of laurolactam ($L_1$), and the content of laurolactam ($L_2$) obtained in the top of the film evaporator of Example 1 was measured to calculate the yield of laurolactam ($L_2/L_1$\*100, %).

\* Method of Measuring Molecular Weight (Polymerization Degree) of PA 12

In the polymerization reactor in which the anionic polymerization reaction was completed, an agitator torque value was calculated, and the value was inversely calculated to calculate the weight average molecular weight of PA 12.

TABLE 1

|  | Laurolactam before purification:ethanol (weight ratio) | Ethanol:water (weight ratio) | LL yield (%) | Residual catalyst content (wt %) | Polymerization degree of PA 12 (weight average molecular weight) |
| --- | --- | --- | --- | --- | --- |
| Example 1 | 1:7 | 1:2.3 | 80% | Trace (undetected) | 10,000 |
| Example 2 | 1:3 | 1:5.3 | 50% | 500 (ppm) | 6,000 |
| Example 3 | 1:7 | 1:1 | 60% | Trace (undetected) | 10,000 |
| Comparative Example 1 | — | — | 90% | 1 (wt %) | Not polymerized |
| Comparative Example 2 | 1:7 | — | 20% | Trace (undetected) | 10,000 |

Referring to Table 1, in Examples 1 to 3, the residual catalyst was substantially removed, and as a result of performing the anionic polymerization reaction using the purified laurolactam, PA 12 was able to be prepared. However, it was confirmed that Example 1 in which LL was purified at a preferred weight ratio of the good solvent and the poor solvent had a more improved yield of LL than Example 3. Meanwhile, in Example 2, ethanol was added in a small amount as compared with the amount of laurolactam before purification, and since laurolactam which is not dissolved in ethanol was removed with the remaining solid catalyst, the LL yield was decreased, and since a material in which laurolactam and a small amount (500 ppm) of the catalyst were agglomerated passed the filter and remained, PA 12 having a low molecular weight (6,000) was prepared. In Comparative Example 1, LL was purified simply by an evaporator without adding the good solvent and the poor solvent of the present invention, and since the activity of the anionic initiator (NaH) of the anionic polymerization reaction was decreased by the catalyst remaining at a high content in the purified LL composition, PA 12 was not able to be polymerized. In addition, in Comparative Example 2, ethanol was added in an excess of water, and a part of LL was not precipitated as a solid and was present in a state of being dissolved in ethanol, and entrainment with ethanol in the evaporator occurred, so that the LL yield was significantly decreased, and thus, it was confirmed that application to a commercial process was difficult.

Hereinabove, although the present invention has been described by specified matters and specific exemplary embodiments, they have been provided only for assisting in the entire understanding of the present invention. Therefore, the present invention is not by the specific matters limited to the exemplary embodiments. Various modifications and changes may be made by those skilled in the art to which the present invention pertains from this description. Therefore, the spirit of the present invention should not be limited to the above-described exemplary embodiments, and the following claims as well as all modified equally or equivalently to the claims are intended to fall within the scope and spirit of the invention.

The invention claimed is:

1. A method of preparing laurolactam, the method comprising:
    a) synthesizing laurolactam by Beckmann rearrangement of cyclododecanone oxime under a catalyst system,
    b) mixing the laurolactam synthesized in a) with a good solvent and removing the catalyst system, and
    c) mixing the laurolactam from which the catalyst system has been removed in b) with a poor solvent and performing recrystallization,
    wherein in c), the laurolactam is recrystallized using a difference in solubility of laurolactam in the good solvent and the poor solvent,
    wherein the good solvent is a c1 to c4 hydrocarbon organic solvent containing one or two or more functional groups selected from the group consisting of a hydroxyl group, an amine group, and a mercapto group, and
    wherein the poor solvent is distilled water or deionized water.

2. The method of preparing laurolactam of claim 1, wherein the Beckmann rearrangement in a) is synthesis of laurolactam from cyanuric chloride by the catalyst system which is cyanuric chloride (TCT) and zinc chloride ($ZnCl_2$), in the presence of a solvent isopropylcyclohexane (IPCH).

3. The method of preparing laurolactam of claim 2, wherein in a), the solvent is removed by distillation.

4. The method of preparing laurolactam of claim 1, wherein in b), the catalyst system is removed using a difference in solubility of the catalyst system and the laurolactam in the good solvent.

5. The method of preparing laurolactam of claim 1, wherein the good solvent and the poor solvent are miscible.

6. The method of preparing laurolactam of claim 1, wherein the good solvent and the poor solvent are injected at a weight ratio of 1:1.5 to 1:3.

7. The method of preparing laurolactam of claim 1, further comprising: evaporating the recrystallized laurolactam to remove heavies in a liquid phase and/or a solid phase and separating laurolactam in a gas phase.

* * * * *